(12) United States Patent
Nakaya et al.

(10) Patent No.: US 11,978,553 B2
(45) Date of Patent: May 7, 2024

(54) INFORMATION RECORDING DEVICE, PROSTHETIC LIMB, ANALYSIS SYSTEM, INFORMATION RECORDING METHOD, AND METHOD OF SUPPORTING PURCHASE OF PRODUCT

(71) Applicant: NABTESCO CORPORATION, Tokyo (JP)

(72) Inventors: Yoshiaki Nakaya, Tokyo (JP); Akio Sakata, Tokyo (JP)

(73) Assignee: NABTESCO CORPORATION, Tokyo (JP)

(*) Notice: Subject to any disclaimer, the term of this patent is extended or adjusted under 35 U.S.C. 154(b) by 533 days.

(21) Appl. No.: 16/720,193

(22) Filed: Dec. 19, 2019

(65) Prior Publication Data

US 2020/0203013 A1 Jun. 25, 2020

(30) Foreign Application Priority Data

Dec. 25, 2018 (JP) .................. 2018-241660

(51) Int. Cl.
| | |
|---|---|
| *G16H 40/67* | (2018.01) |
| *A61B 5/00* | (2006.01) |
| *G06Q 20/12* | (2012.01) |
| *G06Q 30/0601* | (2023.01) |

(52) U.S. Cl.
CPC ........... *G16H 40/67* (2018.01); *A61B 5/4851* (2013.01); *G06Q 20/12* (2013.01); *G06Q 30/0631* (2013.01)

(58) Field of Classification Search
CPC .............................. G16H 40/67; A61B 5/4851
See application file for complete search history.

(56) References Cited

U.S. PATENT DOCUMENTS

| | | | |
|---|---|---|---|
| 8,784,340 B2* | 7/2014 | Sanders | G16H 40/67 600/587 |
| 9,585,019 B2* | 2/2017 | Kawamura | G06Q 30/06 |
| 2009/0222105 A1 | 9/2009 | Clausen | |
| 2010/0023149 A1* | 1/2010 | Sanders | G06F 30/00 700/98 |
| 2013/0261766 A1 | 10/2013 | Langlois et al. | |

(Continued)

FOREIGN PATENT DOCUMENTS

| | | |
|---|---|---|
| JP | 2006129953 A | 5/2006 |
| JP | 5465365 B | 4/2014 |
| JP | 2017182426 A | 10/2017 |

(Continued)

OTHER PUBLICATIONS

EPO Extended Search Report corresponding to Application No. EP19216452.3 dated May 11, 2020.

(Continued)

*Primary Examiner* — Reginald R Reyes
(74) *Attorney, Agent, or Firm* — CANTOR COLBURN LLP

(57) ABSTRACT

An information recording device includes: a sensing unit that senses information related to each of a plurality of functions provided in a product; a storage unit that stores usage information related to use of each of the plurality of functions selected or generated from the information sensed by the sensing unit; and an output unit that outputs the usage information stored in the storage unit.

6 Claims, 10 Drawing Sheets

(56) References Cited

U.S. PATENT DOCUMENTS

2018/0020973 A1   1/2018  Hurley et al.

FOREIGN PATENT DOCUMENTS

| JP | 2018132890 A | 8/2018 |
|---|---|---|
| WO | 03079940 A2 | 10/2003 |
| WO | 2003079940 A3 | 10/2003 |
| WO | 2006069264 A1 | 6/2006 |

OTHER PUBLICATIONS

JPO Notification of Reasons for Refusal for corresponding JP Application No. 2018-241660; dated May 9, 2023.
JPO Notification of Reasons for Refusal for corresponding JP Application No. 2018-241660; dated Nov. 22, 2022.
EPO Office Action for corresponding EP Application No. 19216452.3; dated Aug. 23, 2023.

* cited by examiner

FIG.4

| PRODUCT | WALKING SPEED | PEDOMETER | STANCE FLEXION RESISTANCE FUNCTION | STANCE EXTENSION DAMPER FUNCTION | LOCK FUNCTION | MULTIAXIAL FUNCTION |
|---|---|---|---|---|---|---|
| A | ◎ | ◎ | ◎ | ◎ | ◎ | ◎ |
| B | ◎ | ◎ | × | × | ○ | × |
| C | ◎ | ◎ | ○ | × | × | × |
| D | ○ | ◎ | × | × | × | ◎ |
| E | △ | △ | × | × | △ | ◎ |

INFORMATION RECORDING DEVICE, PROSTHETIC LIMB, ANALYSIS SYSTEM, INFORMATION RECORDING METHOD, AND METHOD OF SUPPORTING PURCHASE OF PRODUCT

CROSS REFERENCE TO RELATED APPLICATIONS

The present application claims priority under 35 U.S.C. § 119 to Japanese Patent Application No. 2018-241660, filed on Dec. 25, 2018, the entire contents of which being incorporated herein by reference.

BACKGROUND OF THE INVENTION

1. Field of the Invention

The present invention relates to an information recording device, a prosthetic limb for which the information recording device can be used, an analysis system for analyzing information recorded by the information recording device, an information recording method, and a method of supporting the purchase of a product by using recorded information.

2. Description of the Related Art

Various prosthetic limbs worn by persons with a partially defective limb to restore the form or function of the limb are provided. The technology to manufacture prosthetic limbs has been improved year by year, and prosthetic limbs provided with various functions capable of improving the quality of life of persons with a partially defective limb have been provided (see, for example, patent literature 1).

Patent literature 1 discloses an artificial knee joint provided with a knee part that is flexed by a multiple-link mechanism and a fluid cylinder for assisting the movement of the knee part in accordance with the flexion angle. In this artificial knee joint, the multiple link mechanism causes the movement of the knee part to simulate the body's knee joint so that the wearer can move naturally. The fluid cylinder supports the walking activity so that walking stability is improved.

[Patent literature 1] JP5465365

Generally, the larger the number of functions installed, the higher the price of the prosthetic limb. Therefore, the user of a prosthetic limb consults a doctor, a prosthetist, a physical therapist, etc. to weigh the function that the user needs and the price of the product and select a product to purchase. It has been difficult to evaluate the function that the user needs in an objective and qualitative manner. Such an issue arises not only in prosthetic limbs but also in other products provided with a plurality of functions.

SUMMARY OF THE INVENTION

The present invention addresses the above-described issue, and a general purpose thereof is to provide a technology capable of adequately knowing the status of use a function provided in a product.

An information recording device according to an embodiment of the present invention includes: an acquisition unit that acquires information related to each of a plurality of functions provided in a product; a storage unit that stores usage information related to use of each of the plurality of functions selected or generated from the information acquired by the acquisition unit; and an output unit that outputs the usage information stored in the storage unit.

A prosthetic limb according to another embodiment of the present invention: a main unit worn on one of limbs of a user; a functional unit that exhibits a function of supporting a physical function of one of the limbs of the user; and an information recording device, wherein the information recording device includes: an acquisition unit that acquires information related to each of a plurality of functions exhibited by the functional unit; a storage unit that stores usage information related to use of each of the plurality of functions selected or generated from the information acquired by the acquisition unit; and an output unit that outputs the usage information stored in the storage unit.

An analysis system according to still another embodiment of the present invention includes: a usage information acquisition unit that acquires the usage information from the above information recording device; an analysis unit that analyzes the usage information acquired by the usage information acquisition unit; and a presentation unit that presents a result of analysis by the analysis unit.

An information recording method according to still another embodiment of the present invention causes a computer to: acquire information related to each of a plurality of functions provided in a product; store, in a storage unit, usage information related to use of each of the plurality of functions selected or generated from the information acquired; and output the usage information stored in the storage unit.

A method of supporting purchase of a product according to still another embodiment of the present invention includes: acquiring usage information recorded when a person interested in a purchase of a product provided with a plurality of functions tries out the product and related to use of each of the plurality of functions; analyzing the usage information; and generating evidence data for proving that the person interested in the purchase needs the function provided in the product, when an application for support to pay for the purchase of the product is filed with an examination authority based on a result of analysis.

Optional combinations of the aforementioned constituting elements, and implementations of the invention replacement of constituting elements in the form of methods, devices, programs, and transitory or non-transitory recording mediums storing programs may also be practiced as optional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 4 shows an example of a function provided in the artificial knee joint;

DETAILED DESCRIPTION OF THE INVENTION

Figure 1:
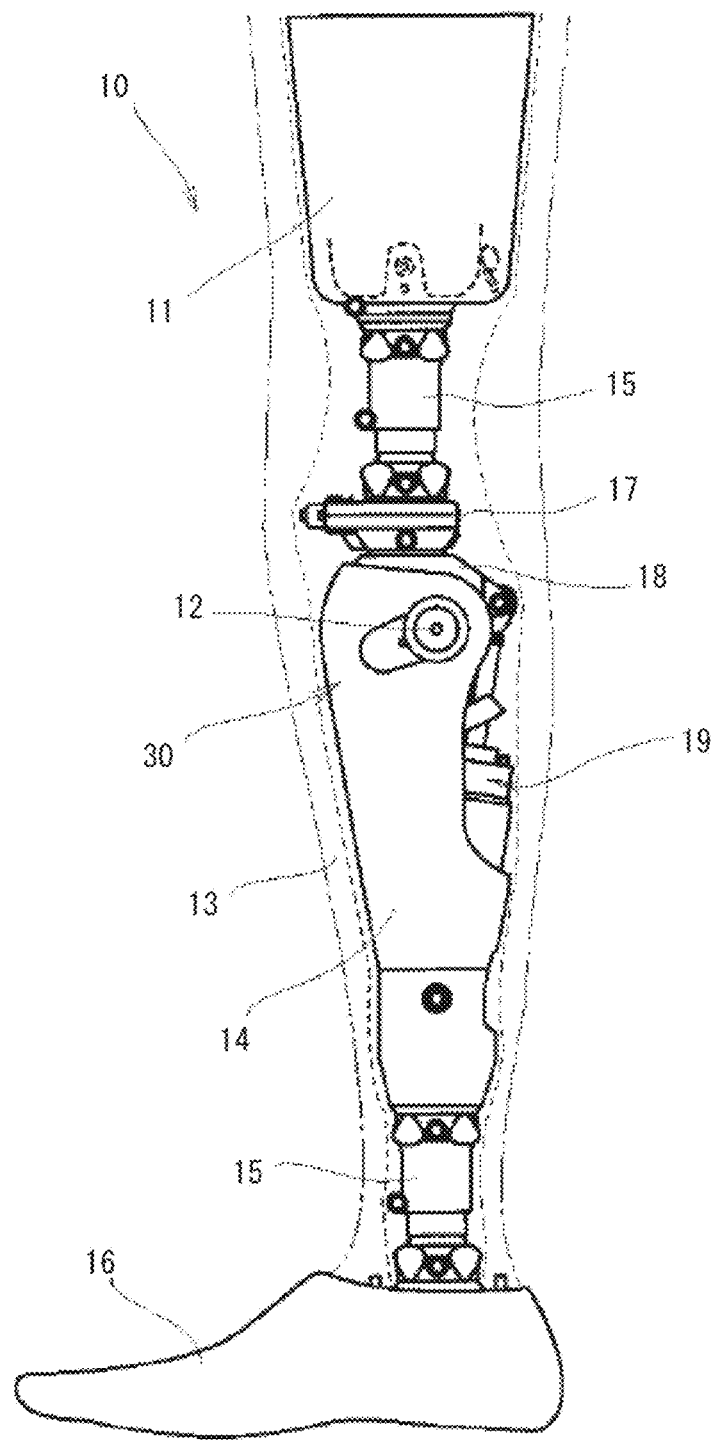
FIG. 1 shows a whole image of an example of prosthetic lower limb provided with a single-axis artificial knee joint.

The invention will now be described by reference to the preferred embodiments. This does not intend to limit the scope of the present invention, but to exemplify the invention.

In the embodiment described in the following, the same constituting elements shall be denoted by the same reference numerals, and duplicative explanations will be omitted appropriately. For convenience of the description, some of the constituting elements are omitted as needed in the drawings.

An embodiment of the present invention will be described by describing a technology of recording information (hereinafter, also referred to as "usage information") related to the use of a plurality of functions provided in a product. A product provided with all of a plurality of installable functions is leased to a person interested in and considering the purchase of the product to let the person try out the product for a predetermined period of time and to record the usage information on the respective functions. By analyzing the recorded usage information, those function required by the person interested in the purchase and those that are not are evaluated in an objective and qualitative manner, and the product suited to the person interested in the purchase is recommended from a lineup of products that differ in the type of functions installed. In this way, convenience for the person interested in the purchase can be improved.

The recorded information can also be used by a manufacturer or a seller of the product to adequately know the status of use of the function by the user of the product and to develop a new product or market the product. For example, the usage information on the function newly installed in the product can be collected for use in improvement and development of the function, sales promotion of the product, etc. In this manner, convenience for the manufacturer and the seller of the product can also be improved.

As mentioned above, a prosthetic limb provided with a large number of functions is relatively expensive. Many purchasers therefore purchase a prosthetic limb by receiving the benefit of a public fund, insurance payment, money granted from an enterprise, etc. Application for support to pay for the purchase often requires submitting an evaluation report by a prosthetist or a doctor to prove the necessity of the prosthetic limb, but it has been difficult to present objective and qualitative evidence. Also, the criterion for determining acceptance or non-acceptance of the application has been vague, and an examination authority examining applications has also required a criterion for determining acceptance or non-acceptance of applications objectively based on qualitative evidence. According to the technology of the embodiment, it is possible to generate, from the usage information, evidence data for proving that the person interested in the purchase needs the function provided in the prosthetic limb considered for purchase and to submit the data to the examination authority. Therefore, the examination authority can determine acceptance or non-acceptance of the application easily and objectively based on the clear criterion that uses the qualitative evidence data. Accordingly, the technology according to the embodiment not only improves convenience for the user of the product or the person interested in the purchase but is also helpful for the examination authority that examines applications for support to pay for the purchase of the product.

In the following embodiment, a prosthetic limb and, in particular, a prosthetic lower limb provided with an artificial knee joint, will be described by way of one example of product provided with a plurality of functions. An artificial knee joint is exemplified by a single-axis knee artificial joint provided with a single-axis knee part and a multiple-link artificial knee joint provided with a knee part having a multiple-link mechanism. A brief description will first be given of these features.

FIG. 1 shows a whole image of an example of prosthetic lower limb provided with a single-axis artificial knee joint. An above-knee prosthesis 10 is provided with a resin socket 11 for accommodating the amputated end, an artificial knee joint 30 for providing a function for flexion-extension of the knee, and a foot part 16 that touches the ground. The above-knee prosthesis 10 is also provided with an adaptor 15 with an adjustable length and a rotary joint 17 that enables rotation around an axial line in order to adapt the length of the prosthetic lower limb in the axial line direction to the wearer. These constituting members are covered by an outer cover 13 in a leg form.

In a view of the artificial knee joint 30, the above-knee prosthesis 10 is provided with a knee shaft 12 rotatably coupling a first constituting member (knee member) 18 on the thigh side and a second constituting member (frame member) 14 on the lower leg side. The above-knee prosthesis 10 is also provided with a cylinder device 19 as a fluid pressure control device for supporting the function for flexion-extension.

Figure 2:
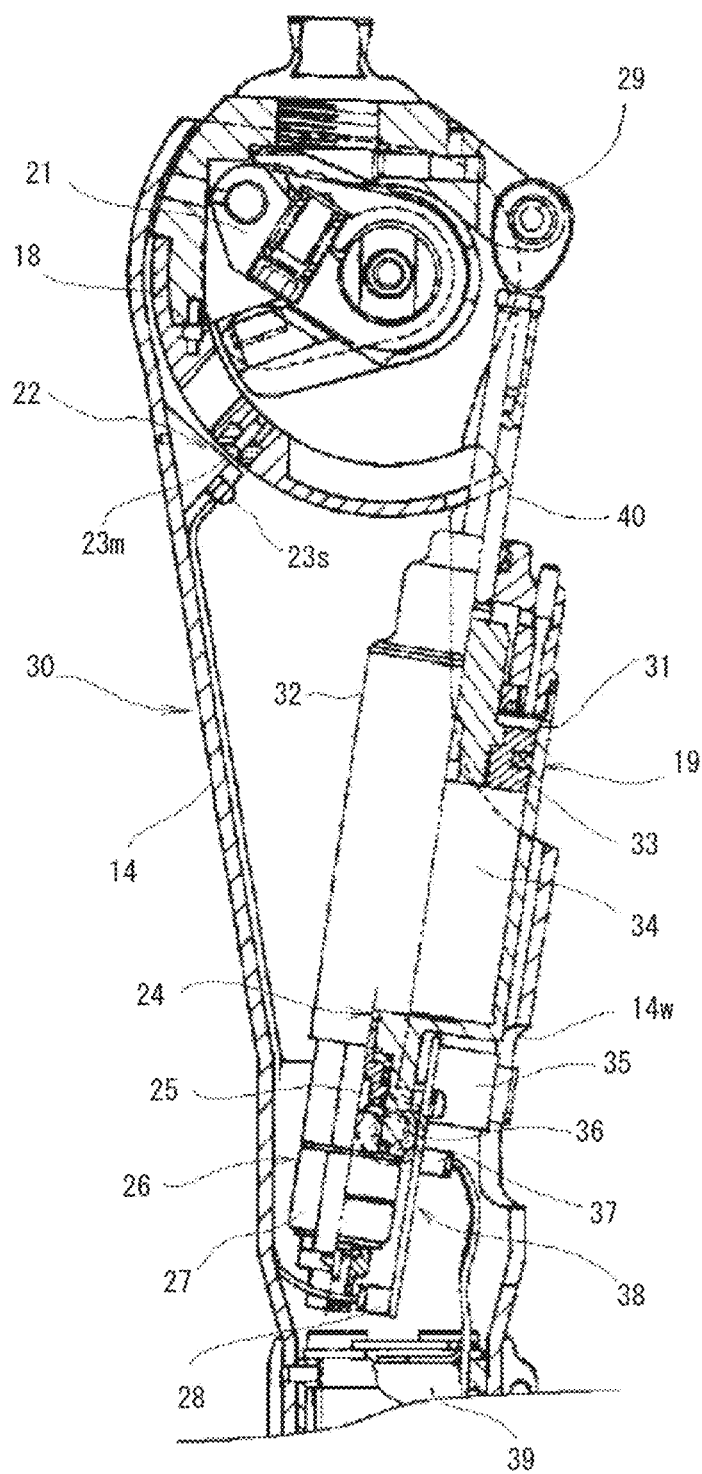
FIG. 2 shows a cross-sectional structure of a part of the artificial knee joint.

FIG. 2 shows a cross-sectional structure of a part of the artificial knee joint 30. Toward the top of the interior of the frame member 14 of the artificial knee joint 30 are provided a brake mechanism 21 located around the knee shaft 12 and a sensor 22 that includes a magnet 23m on the side of the knee member 18 and a proximity switch 23s on the side of the frame member 14. Further, the cylinder device 19 has a first point of support 29 at one end of a piston rod 40 and a second point of support 36 below a tube-shaped cylinder main body 32 that is a housing member. The piston rod 40 supports a piston 33 as a partition member inside the cylinder main body 32. The piston 33 partitions the interior of the cylinder main body 32 into a first chamber 31 and a second chamber 34. When the knee is flexed or extended, air is caused to flow between the first chamber 31 and the second chamber 34. A communication passage that communicates with the first chamber 31 and the second chamber 34 is located in the piston 33 and in the cylinder main body 32. The communication passages are parallel to each other. A variable control valve 24 with a variable valve position or opening is provided in the middle of the communication passage in the cylinder main body 32. The variable control valve 24 is a valve for providing resistance to the flexion of the knee. The more open the valve is, the smaller the resistance to the flexion. Conversely, the less open, the larger the resistance to the flexion.

The variable control valve 24 is a needle valve, and the valve position can be changed by moving the needle in the axial line direction. A driving mechanism 26 moves the needle of the variable control valve 24. The driving mechanism 26 is provided with an electronically controllable stepping motor 27 and a thread part 25 that transforms the rotation of the stepping motor 27 into a linear movement. The linear movement produced by the thread part 25 moves the needle of the variable control valve 24 in the axial line direction.

The driving mechanism 26 is located toward the cylinder bottom of the cylinder device 19. An electronic control circuit 38 for providing a control command to the driving mechanism 26 is provided toward the cylinder bottom. The electronic control circuit 38 is provided with a power supply terminal 37 for connection to a battery 39, a connector 35 for configuring control data suited to each wearer of the prosthetic lower limb, and, further, a sensor terminal 28 for receiving a signal from the sensor 22 (i.e., a sensor for detecting a walking speed) comprised of the magnet 23m and the proximity switch 23s.

Figure 3:
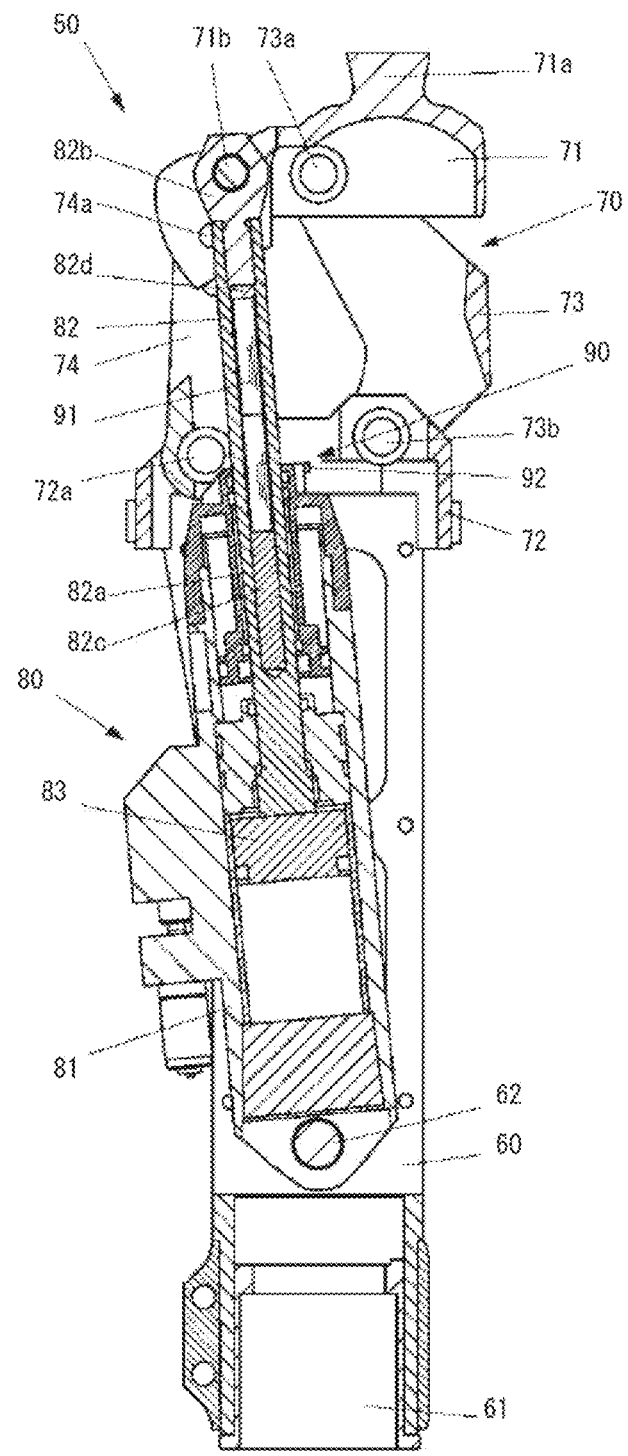
FIG. 3 shows an example of a multiple-link artificial knee joint.

FIG. 3 shows an example of a multiple-link artificial knee joint. A four-link artificial knee joint 50 is provided with a frame 60, a knee part 7 having a four-link mechanism, a fluid cylinder 80 that is a cylinder that uses oil as a working fluid and restricts the action of the knee part 70 by generating a drag, a driving device 93 for varying the characteristics of the fluid cylinder 80, a position detection device 90 as an extension/contraction magnitude detection means for detecting the position a piston rod 82 relative to a cylinder tube 81 of the fluid cylinder 80 as indicating the magnitude of extension/contraction of the fluid cylinder 80, a signal processing circuit 94 for processing a signal output from the position detection device 90, a computer 95 for controlling the characteristics (the magnitude of the drag generated) of the fluid cylinder 80 by controlling the operation of the driving device 93, and a battery (not shown) for supplying power to the components such as the driving device 93, the signal processing circuit 94, and the computer 95.

It should be noted that the driving device 93, the signal processing circuit 94, the computer 95, and the battery are not shown in FIG. 3 but are actually fitted to the frame 60 or the fluid cylinder 80.

The knee part 70 is fixed to the frame 60. The frame 60 is provided a foot connection part 61 (not shown) for connection to the pipe of the foot part (not shown) at the end opposite to the side provided with the knee part 70. The frame 60 is also provided with a shaft 62 that rotatably supports the cylinder tube 81. The four-link artificial knee joint 50 and the foot part are assembled to form a prosthetic lower limb.

The knee part 70 is provided with an upper link 71 provided with a thigh connection part 71a for connection to the thigh-side socket of the user of the prosthetic lower limb, a lower link 72 fixed to the frame 60, a front link 73 coupled to the upper link 71 and the lower link 72, and a rear link 74 coupled to the upper link 71 and the lower link 72. The upper link 71 is provided with a shaft 71b that rotatably supports the piston rod 82. The lower link 72 is provided with a shaft 72a that rotatably supports the rear link 74. The front link 73 is provided with a shaft 73a that rotatably supports the upper link 71 and a shaft 73b that rotatably supports the lower link 72. The rear link 74 is provided with a shaft 74a that rotatably supports the upper link 71.

The shaft 71b is provided above the line connecting the shaft 73a and the shaft 74a. Further, the shaft 62 that rotatably supports the cylinder tube 81 is provided in the lower part of the frame 60. Therefore, the fluid cylinder 80 is accommodated inside the frame 60 such that it can be extended, contracted, or oscillated.

The fluid cylinder 80 is provided with a cylinder tube 81, a piston rod 82 movable with respect to the cylinder tube 81, and a piston rod 83 movably accommodated in the cylinder tube 81 and having the piston rod 82 fixed thereto. The piston rod 82 is made of a non-magnetic material. Further, the piston rod 82 is provided with a rod main body 82a in which a space for accommodating a magnet 91 described later is formed, a rod end 82b fixed to the rod main body 82a, and spacers 82c, 82d adjusted to a predetermined length to sandwich and fix the magnet 91 in the piston rod 82. A female thread is formed in the rod main body 82a. A male thread combined with the female thread of the rod main body 82a is formed in the rod end 82b.

The position detection device 90 is provided with the magnet 91 accommodated in the piston rod 82 and a magnetic sensor 92 fixed to the cylinder tube 81 to detect the position of the magnet 91. The magnet 91 is, for example, an alnico magnet. The magnetic sensor 92 is a sensor for detecting the position of the magnet 91 according to the magnitude of magnetic field that the magnet 91 generates and is, for example, a Hall element.

The piston rod 82 is configured such that the spacer 82c, the magnet 91, and the spacer 82d are sequentially accommodated in the rod main body 82a, and then the magnet 91 is fixed at a predetermined position inside by fastening the male thread of the rod end 82b and the female thread of the rod main body 82a.

The computer 95 is, for example, a micro control unit (MCU). The computer 95 is configured to obtain the flexion angle of the knee part 70, i.e., the angle of flexion (or extension) of the four-link artificial knee joint 50 relative to the thigh of the user of the prosthetic lower limb connected to the thigh connection part 71a, by transforming the position detected by the magnetic sensor 92.

FIG. 4 shows an example of a function provided in the artificial knee joint. Functions installable in the artificial knee joint as described above include, for example, a walking speed adjusting function, stance flexion resistance function, stance extension damper function, lock function, and multiaxial function. Product A is the highest-end product provided with all of the functions and is most expensive among products A-E. Products B-E are mid-range or low-end products provided with only some of the functions and priced lower than product A. The user of the prosthetic lower limb considers the function that he or she needs and the price of the product and selects a product to purchase from a lineup of a plurality of products. For the purpose of supporting the purchase of a product by the user of the prosthetic lower limb, the analysis system according to the embodiment records usage information for each function collected when product A provided with all functions is tried out by the user, identifies the function needed by the user by analyzing the recorded usage information, and recommends a product suited to the user. Further, the analysis system generates a report to which is attached evidence data for proving that the user needs a particular function in an objective and qualitative manner.

Figure 5:
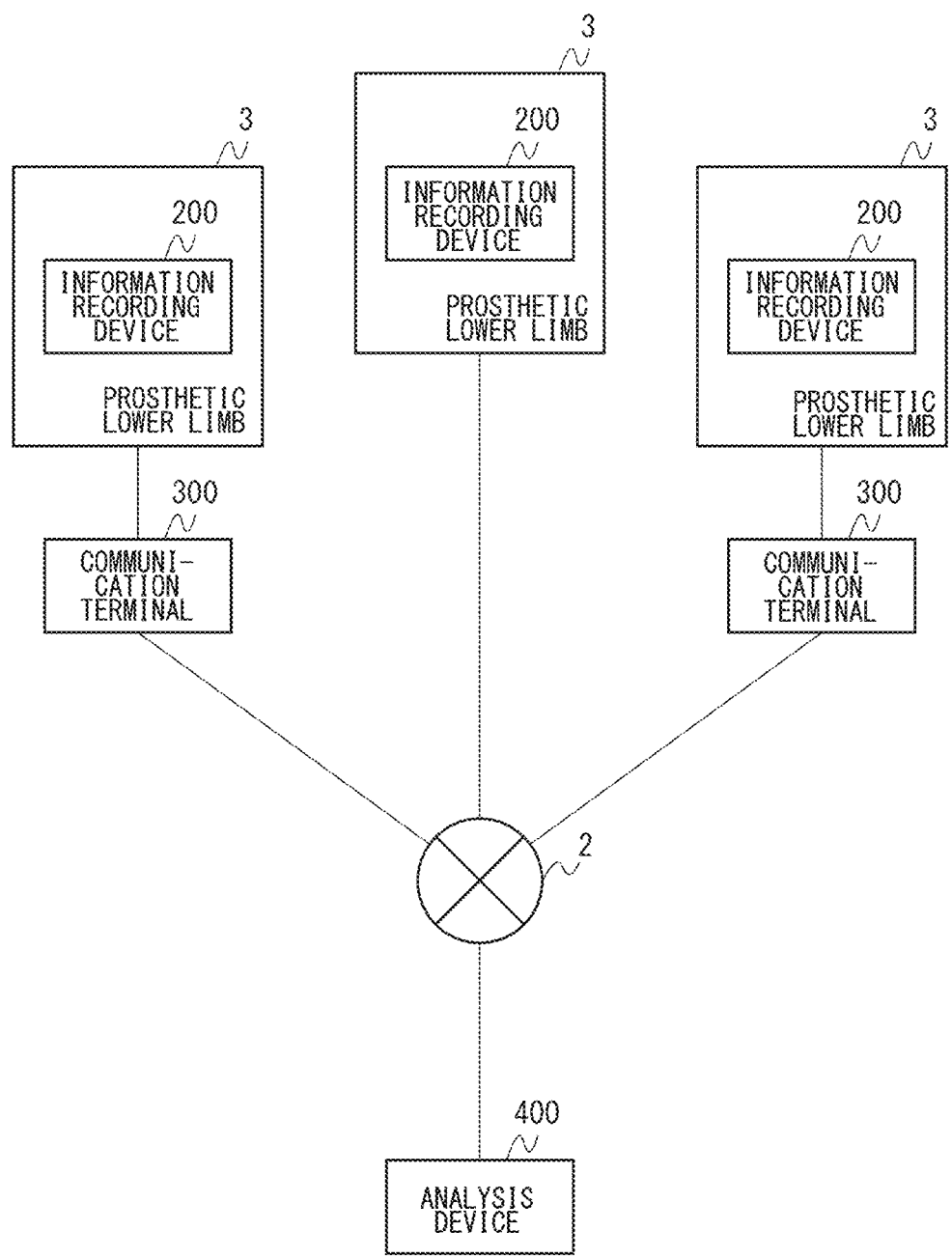
FIG. 5 shows a configuration of the analysis system according to the embodiment.

FIG. 5 shows a configuration of the analysis system according to the embodiment. The analysis system 1 is provided with an information recording device 200 built in a prosthetic lower limb 3 to record usage information on a plurality of functions provided by the prosthetic lower limb 3, a communication terminal 300 that transmits the usage information recorded in the information recording device 200 to an analysis device 400, an analysis device 400 that analyzes the usage information, and the Internet 2 exemplifying a communication network connecting these devices. In the case the prosthetic lower limb 3 or the information recording device 200 includes a communication function, the usage information may be directly transmitted to the analysis device 400 without being mediated by the communication terminal 300.

The analysis device 400 acquires the usage information from a plurality of information recording devices 200 built in a plurality of prosthetic lower limbs 3, respectively, and analyzes the usage information for each user. The analysis device 400 also accumulates the usage information on a plurality of users and analyzes the resultant big data.

Figure 6:
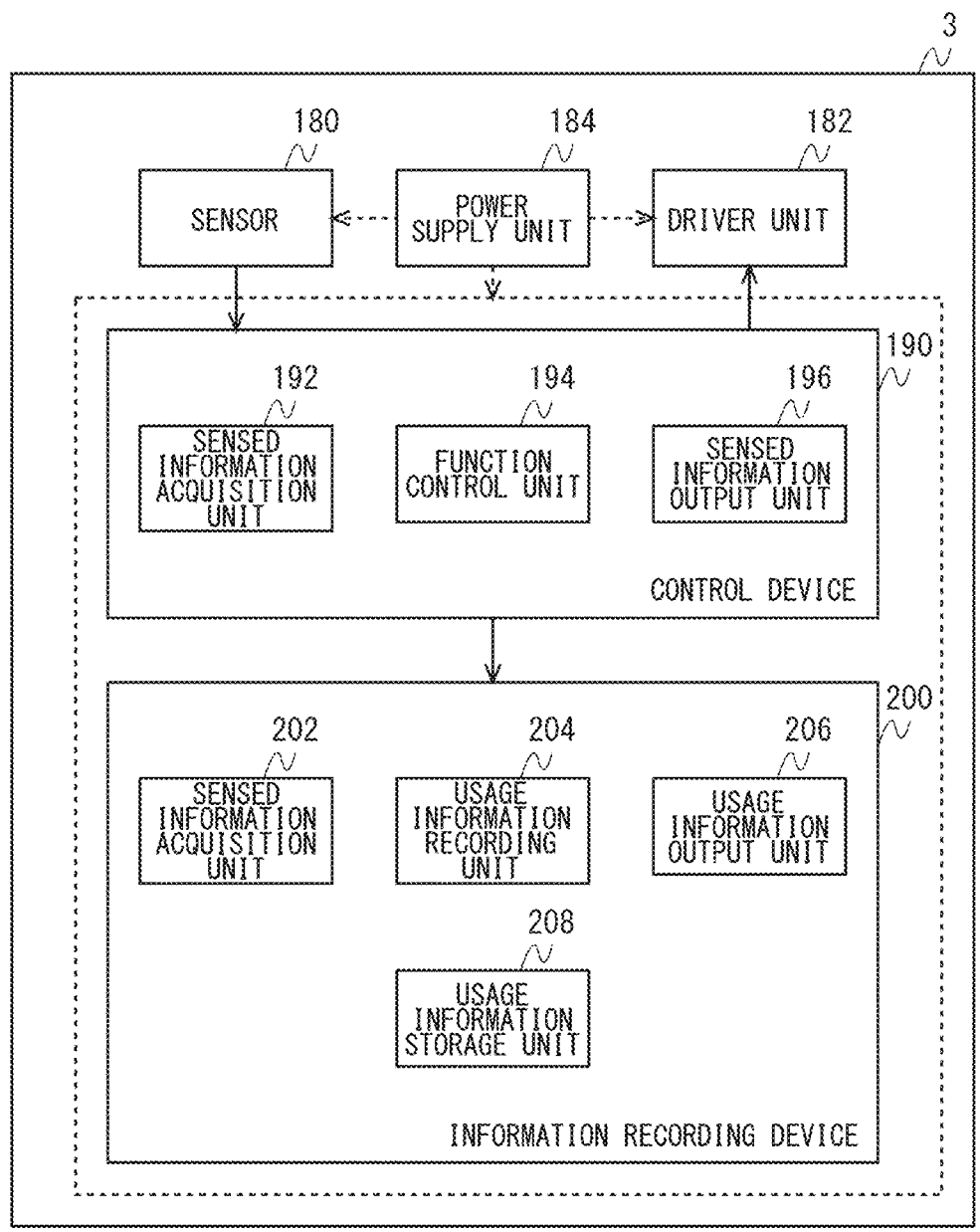
FIG. 6 is a block diagram showing functions and a configuration of the prosthetic lower limb.

FIG. 6 is a block diagram showing functions and a configuration of the prosthetic lower limb 3. The blocks depicted in the block diagram of this specification are implemented in hardware such as devices like a CPU of a computer or mechanical components, and in software such as a computer program etc. FIG. 6 depicts functional blocks implemented by the cooperation of these elements. Therefore, it will be understood by those skilled in the art that the functional blocks may be implemented in a variety of manners by a combination of hardware and software.

The prosthetic lower limb 3 is provided with a sensor 180, a driver unit 182, a control device 190, the information recording device 200, and a power supply unit 184 for supplying power to these components.

The sensor 180 senses various information used by the control device 190 to execute the functions provided in the prosthetic lower limb 3. The sensor 180 is, for example, the sensor 22 of the artificial knee joint shown in FIG. 2. Alternatively, the sensor 180 may be software for sensing that the function control unit 194 controls a function. Any of various sensors inherently provided in the prosthetic lower limb 3 to execute the function of the prosthetic lower limb 3 may be used as the sensor 180.

The driver unit 182 is an example of a functional unit that exhibits a function provided in the prosthetic lower limb 3 and drives the components of the prosthetic lower limb 3. The driver unit 182 is controlled by the function control unit 194 of the control device 190.

The control device 190 is provided with a sensed information acquisition unit 192, the function control unit 194, and a sensed information output unit 196.

The sensed information acquisition unit 192 acquires the information sensed by the sensor 180. The function control unit 194 controls a component such as the driver unit 182 in order to exhibit the plurality of functions provided in the prosthetic lower limb 3, based on the sensed information acquired by the sensed information acquisition unit 192. The sensed information output unit 196 outputs the sensed information to the information recording device 200.

The information recording device 200 is provided with a sensed information acquisition unit 202, a usage information recording unit 204, a usage information output unit 206, and a usage information storage unit 208.

The usage information storage unit 208 stores the usage information selected or generated from information related to the function. The usage information may indicate, for example, whether an associated function is used or not, the number of times that the function is used, the duration of use, the time when the function is used, etc. The duration of use may include the accumulated duration of use, the maximum continuous duration of use, the minimum continuous duration of use, the average continuous duration of use, etc. The usage information may include sensed information used to control an associated function. The usage information may include information indicating the usage mode or the status of use of the function. The information indicating the usage mode or the status of use of the function may include the value of a control variable for controlling the function, the amount of driving by the driver unit, etc. The usage information storage unit 208 may store the usage information in a ring buffer scheme or the like. In this case, when the usage information is stored beyond the capacity of the ring buffer, the usage information is sequentially deleted such that the oldest information is deleted first. In the case the prosthetic lower limb 3 provided with the information recording device 200 is leased to a plurality of persons interested in the purchase, the usage information stored in the usage information storage unit 208 may be deleted when the user of the prosthetic lower limb 3 is changed. The usage information stored in the usage information storage unit 208 may be deleted when an instruction to reset the usage information storage unit 208 is provided from the use or the communication terminal 300, etc. Alternatively, the usage information may be deleted when it is sensed that the user has changed. The usage information storage unit 208 may store the usage information temporarily, and the usage information may be deleted when it is output from the usage information output unit 206 to the communication terminal 300 or the analysis device 400.

The sensed information acquisition unit 202 acquires the sensed information from the control device 190. The usage information recording unit 204 selects or generates the usage information that should be stored in the usage information storage unit 208 from the sensed information acquired by the sensed information acquisition unit 202 and records the selected or generated information in the usage information storage unit 208. As will be described later, the usage information recording unit 204 selects or generates the usage information by executing a recording program delivered from the analysis device 400. All of the sensed information acquired by the sensed information acquisition unit 202 may be recorded in the usage information storage unit 208. In that case, the recording program for selecting or generating the usage information from the sensed information may not be provided.

The usage information output unit 206 reads the usage information from the usage information storage unit 208 at a predetermined point of time and outputs the usage information to the communication terminal 300 or the analysis device 400. For example, the usage information output unit 206 may output the usage information periodically at predetermined time intervals, output the usage information when a predetermined trial period expires, or output the usage information when the communication terminal 300 of the analysis device 400 requests an output.

Figure 7:
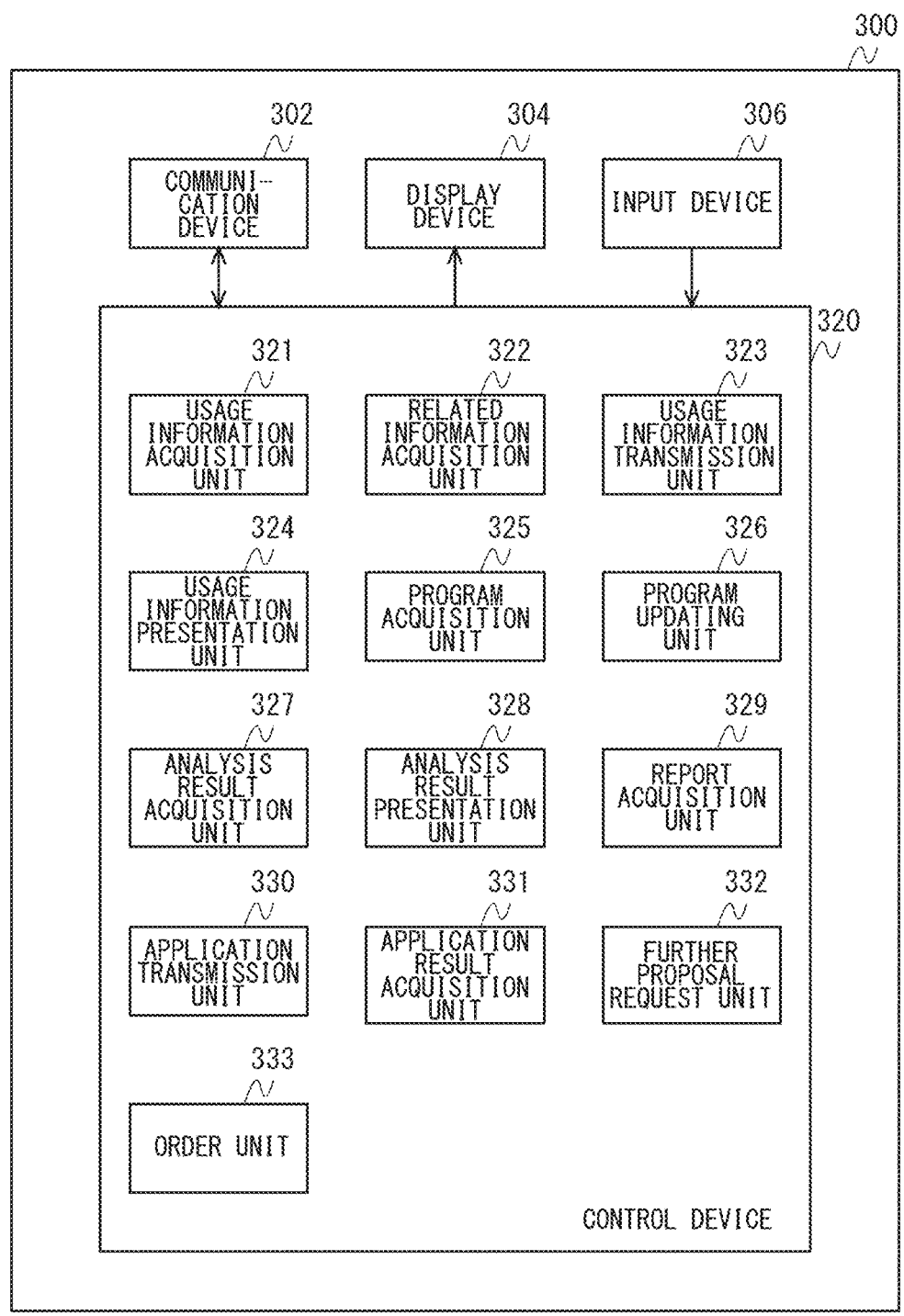
FIG. 7 is a block diagram showing functions and a configuration of the communication terminal according to the embodiment.

FIG. 7 is a block diagram showing functions and a configuration of the communication terminal 300 according to the embodiment. The blocks shown in the figure can be implemented in a variety of manners by a combination of hardware and software. The communication terminal 300 exemplifies an external communication device and may be a cellular phone terminal, a smartphone, a tablet terminal, a personal computer, etc. that the user of the prosthetic lower limb 3 or the person interested in the purchase uses.

The communication terminal 300 is provided with a communication device 302, a display device 304, an input device 306, and a control device 320.

The communication device 302 controls communication with another device. The communication device 302 may communicate in an arbitrary wired or wireless communication scheme. The display device 304 displays a screen generated by the control device 320. The display device 304 may be a liquid crystal display device, an organic EL display device, etc. The input device 306 transmits a command input by the user of the prosthetic lower limb 3 or the person interested in the purchase to the control device 320. The input device 306 may be a mouse, a keyboard, a touch pad, etc. The display device 304 and the input device 306 may be implemented as a touch panel.

The control device 320 is provided with a usage information acquisition unit 321, a related information acquisition unit 322, a usage information transmission unit 323, a usage information presentation unit 324, a program acquisition unit 325, a program updating unit 326, an analysis result acquisition unit 327, an analysis result presentation unit 328, a report acquisition unit 329, an application transmission unit 330, an application result acquisition unit 331, a further proposal request unit 332, and an order unit 333.

The usage information acquisition unit 321 acquires the usage information from the information recording device 200. The related information acquisition unit 322 acquires information (hereinafter, also referred to as "related information") related to the use of the prosthetic lower limb 3 that can be acquired from a device or equipment other than the prosthetic lower limb 3. The related information is information different from the usage information and recorded in the information recording device 200 when the prosthetic lower limb 3 is used. The related information is additionally referred to by the analysis device 400 to analyze the usage mode and the status of use of the prosthetic lower limb 3. The related information may include information useful for the analysis device 400 to analyze the usage mode and the status of use of the prosthetic lower limb 3, including: attribute information such as age, sex, weight, height, muscular strength, and medical history of the person interested in the purchase who has tried out the prosthetic lower limb 3; measurements such as heart rate, body temperature, and blood pressure of the person interested in the purchase; meteorological information such as temperature, humidity, and weather; environmental information such as room plan at home or place of work, daily used transportation/facility/migration pathway/places of visit of the person interested in the purchase; position information indicating the position of the person interested in the purchase who is trying out the prosthetic lower limb; and images of surrounding areas. In the case the person interested in the purchase has an experience of using a prosthetic lower limb, the related information may include the length of the prosthetic lower limb, length of the foot, length of the amputated end, level of amputation, amputated limb, activity level, history of use of prosthetic lower limbs, and reason for amputation. The usage information transmission unit 323 appends the related information acquired by the related information acquisition unit 322 to the usage information acquired by the usage information acquisition unit 321 and transmits the resultant information to the analysis device 400. The usage information presentation unit 324 displays the usage information and the related information on the display device 304 for presentation to the purchaser. The related information may be transmitted to the prosthetic lower limb 3 and used to control the prosthetic lower limb 3, for example.

The program acquisition unit 325 acquires, from the analysis device 400, a recording program used by the usage information recording unit 204 of the information recording device 200 to select or generate the usage information. When the recording program delivered from the analysis device 400 is updated, the program updating unit 326 transmits the recording program acquired by the program acquisition unit 325 to the information recording device 200 to update the program. In this way, the recording program can be updated to allow the information recording device 200 to record necessary usage information even when the usage information used by the analysis device 400 for analysis is changed, or when the specification of a report submitted to apply for the purchase of the prosthetic lower limb 3 is changed.

The analysis result acquisition unit 327 acquires the analysis result from the analysis device 400. The analysis result may include, for example, a combination of functions that the person interested in the purchase needs, information on the prosthetic lower limb 3 product provided with the combination of the functions, etc. The analysis result presentation unit 328 displays the analysis result acquired by the analysis result acquisition unit 327 on the display device 304 for presentation to the person interested in the purchase. This allows the person interested in purchasing the prosthetic lower limb 3 to consider a product to purchase from the lineup of prosthetic lower limbs 3 by referring to the analysis result based on the usage information collected when the prosthetic lower limb 3 is actually used. Accordingly, the person can select a proper product easily and adequately.

The report acquisition unit 329 acquires, from the analysis device 400, a report to submit to the examination authority such as a government when the person, interested in the purchase desiring to receive support to pay for the purchase of the prosthetic lower limb 3, applies for support for the purchase of the prosthetic lower limb 3. The report shows the analysis result of the usage information as evidence data for proving that the person interested in the purchase needs the function provided in the prosthetic lower limb 3 desired to be purchased. This allows highly reliable, objective, and qualitative evidence data based on the usage information collected when the prosthetic lower limb 3 is actually used to be attached to the application and so can appeal the need for the function to the examination authority persuasively. It also reduces the load on the prosthetist drafting the report significantly. It also helps clarify the examination criterion, which has been vague in the related art, and allows the examination authority to examine applications more easily and in a more objective manner. This allows the limited budget to be distributed more properly to persons interested in the purchase.

The application transmission unit 330 transmits the report acquired by the report acquisition unit 329 to the examination authority and transmits information necessary for application for support to pay for the purchase to the examination authority. A plurality of candidates of prosthetic lower limbs 3 may be explicitly listed in the report in one application in the order of suitability. The examination authority compares and evaluates the plurality of candidates of prosthetic lower limbs 3 based on the submitted report and the evidence data attached to the report. The examination authority determines to accept the purchase of one of the plurality of candidates or not to accept any of the candidates. The application result acquisition unit 331 acquires the result of examination of the application from the examination authority. In the case none of the plurality of candidates of prosthetic lower limbs 3 applied for is accepted, the further proposal request unit 332 requests the analysis device 400 for a further proposal of a recommended prosthetic lower limb 3. The analysis result acquisition unit 327 acquires the information on the prosthetic lower limb 3 suggested to be purchased in the further proposal. The analysis result presentation unit 328 presents the analysis result acquired by the analysis result acquisition unit 327. The report acquisition unit 329 acquires a report on the prosthetic lower limb 3 product suggested to be purchased in the further proposal. The application transmission unit 330 applies, for a second time, for support to pay for the purchase of the prosthetic lower limb 3 suggested to be purchased in the further proposal. If the application is accepted, the order unit 333 orders the prosthetic lower limb 3 from a prosthetic limb factory or the manufacturer of prosthetic limbs. The functions of the application transmission unit 330, the application result acquisition unit 331, the further proposal request unit 332, and the order unit 333 may be executed automatically online or executed according to an instruction of the purchaser. Alternatively, these features may not be provided.

Figure 8:
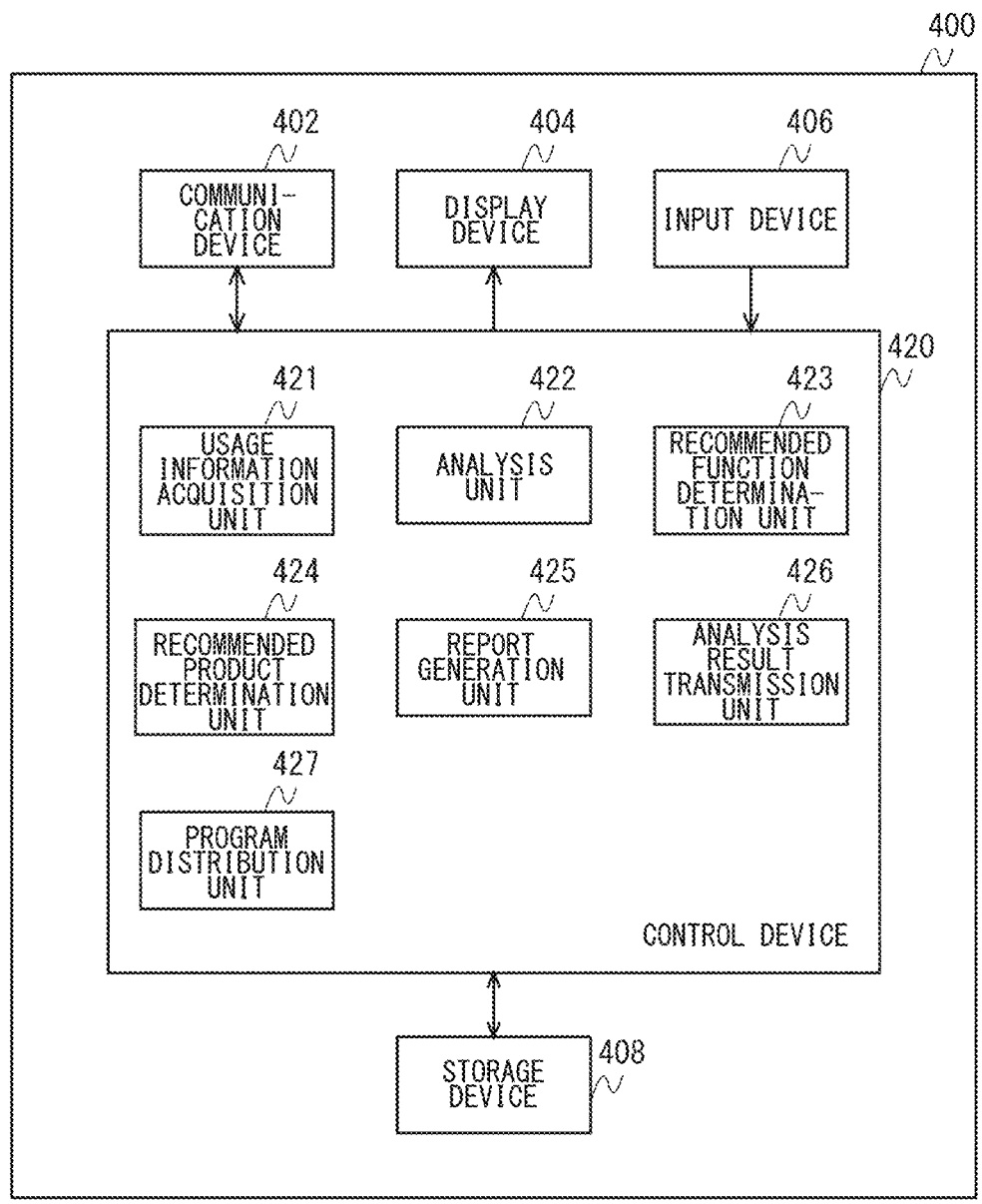
FIG. 8 is a block diagram showing functions and a configuration of the analysis device according to the embodiment.

FIG. 8 is a block diagram showing functions and a configuration of the analysis device 400 according to the embodiment. The blocks shown in the figure can also be implemented in a variety of manners by a combination of hardware and software. The analysis device 400 may be implemented by a server device, a personal computer, etc.

The analysis device 400 is provided with a communication device 402, a display device 404, an input device 406, a storage device 408, and a control device 420.

The communication device 402 controls communication with another device. The communication device 402 may communicate in an arbitrary wired or wireless communication scheme. The display device 404 displays a screen generated by the control device 420. The display device 404 may be a liquid crystal display device, an organic EL display device, etc. The input device 406 transmits a command input by the analyst to the control device 420. The input device 406 may be a mouse, a keyboard, a touch pad, etc. The display device 404 and the input device 406 may be implemented as a touch panel.

The storage device 408 stores various data and programs used by the control device 420. The storage device 408 stores, for example, the product information on the prosthetic lower limb 3, the format of a report, the recording program delivered to the information recording device 200, etc. Further, the storage device 408 accumulates the usage information recorded by the plurality of information recording devices 200. The analysis device 400 may acquire the result of application filed with the examination authority, the information on the prosthetic lower limb actually purchased by the user, etc. from the communication terminal 300 and accumulate the information in the storage device 408.

The control device 420 is provided with a usage information acquisition unit 421, an analysis unit 422, a recommended function determination unit 423, a recommended product determination unit 424, a report generation unit 425, an analysis result transmission unit 426, and a program delivery unit 427.

The usage information acquisition unit 421 acquires the usage information from the information recording device 200 or the communication terminal 300 and stores the information in the storage device 408. The analysis unit 422 analyzes the usage information acquired from the usage information acquisition unit 421. The recommended function determination unit 423 determines the function of the prosthetic lower limb recommended to the person interested in the purchase of the prosthetic lower limb, based on the result of analysis by the analysis unit 422. The recommended product determination unit 424 determines a product provided with the function determined by the recommended function determination unit 423 as a recommended product. The report generation unit 425 generates a report that the person interested in the purchase submits to the examination authority to apply for support to pay for the purchase, based on the result of analysis of the usage information. The analysis result transmission unit 426 transmits the analysis result such as the recommended function, the recommended product, and the report to the communication terminal 300.

In the case the examination criterion for applications, format of a report that should be submitted, type and form of evidence data, etc. in the examination authority varies from one examination authority to another, the usage information acquisition unit 421 may further acquire information on the government or examination authority with which an application for support to pay for the purchase is submitted and store the information in the storage device 408. In this case, the analysis unit 422, the recommended function determination unit 423, the recommended product determination unit 424, and the report generation unit 425 further refer to the government or examination authority with which to file the application and analyze the usage information, determine the recommended function or recommended product, or generate a report.

The analysis unit 422 may not only analyze the usage information on the person interested in the purchase as an individual but also analyze the usage information on a plurality of persons interested in the purchase. The analysis result transmission unit 426 may transmit a result showing a comparison between the usage information of the person interested in the purchase as an individual and the usage information on the plurality of other persons interested in the purchase to the communication terminal 300 and cause the result to be presented. For example, the analysis result transmission unit 426 may present where the frequency of use of a particular function of a given person interested in the purchase is found in the entire distribution of the persons interested in the purchase. This makes it possible to know the necessity of the function in more objective and quantitative manner.

When the recording program stored in the storage device 408 is updated, the program delivery unit 427 delivers the recording program to the information recording device 200. The program delivery unit 427 may deliver the recording program to the communication terminal 300 by using an application delivery service that works on a smartphone. In the case the recording program is delivered to a personal computer etc., the program delivery unit 427 may notify the destination personal computer etc. of an update to the recording program.

Figure 9:
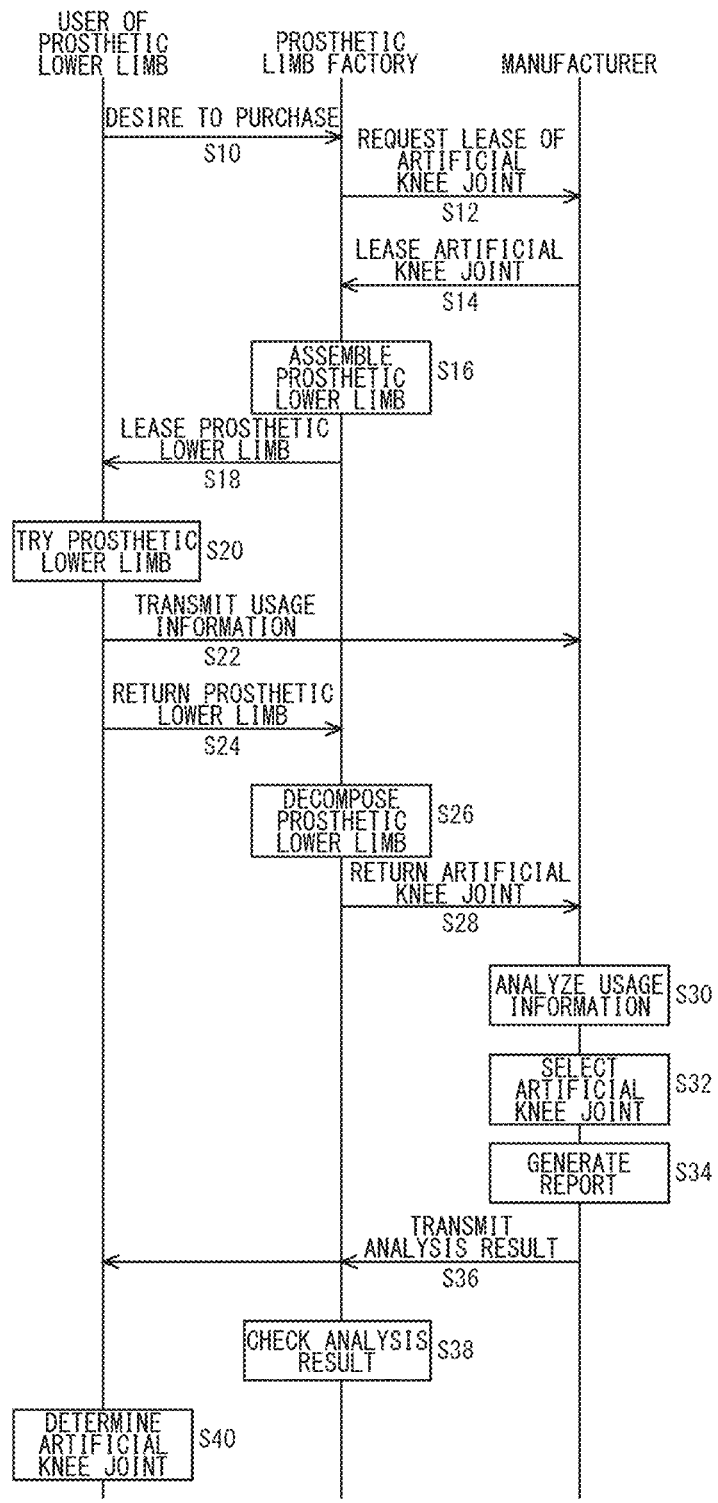
FIG. 9 is a sequence chart showing the steps of the product purchase supporting method according to the embodiment.

FIG. 9 is a sequence chart showing the steps of the product purchase supporting method according to the embodiment. The figure shows the steps performed until a prosthetic lower limb user determines a prosthetic lower limb desired to be purchased and includes the steps of the information recording method according to the embodiment. When the user of a prosthetic lower desires to purchase a prosthetic lower limb from a prosthetic limb factory (S10), the prosthetic limb factory requests the manufacturer of prosthetic lower limbs to lease an artificial knee joint (S12). The manufacturer leases the highest-end artificial knee joint having the above-described information recording device 200 built in and provided with all of the installable functions to the prosthetic limb factory (S14). The prosthetic limb factory assembles a prosthetic lower limb provided with the artificial knee joint thus leased (S16) and leases the prosthesis to the prosthetic lower limb user (S18). The prosthetic lower limb user tries out the prosthetic lower limb thus leased in a daily life (S20). While the prosthesis is being tried out, the information recording device 200 built in the prosthetic lower limb records usage information. When the lease period expires, the usage information is transmitted to the analysis device 400 of the manufacturer (S22). When the prosthetic lower limb is returned from the prosthetic lower limb user (S24), the prosthetic limb factory decomposes the prosthetic lower limb (S26) and returns the leased artificial knee joint to the manufacturer (S28). The analysis device 400 analyzes the usage information (S30), determines the function that the prosthetic lower limb user needs, and selects an artificial knee joint provided with the determined function (S32). The analysis device 400 generates a report to submit to the examination authority (S34) and transmits the report to the prosthetic limb factory and the prosthetic lower limb user along with the analysis result (S36). The prosthetic limb factory checks the analysis result transmitted from the analysis device 400 (S38). When there is no problem, the prosthetic lower limb user determines an artificial knee joint to purchase (S40).

Figure 10:
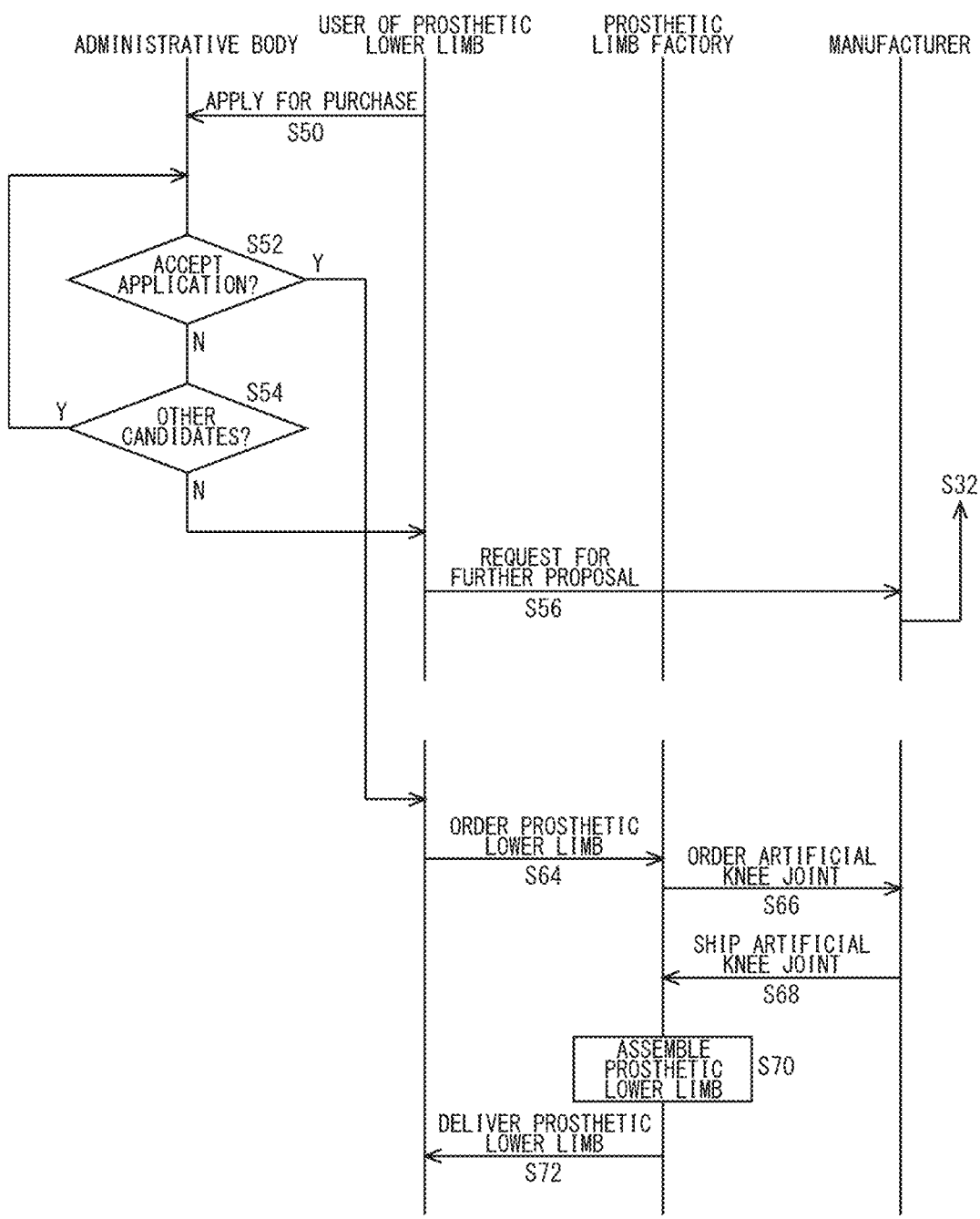
FIG. 10 is a sequence chart showing the steps of the product purchase supporting method according to the embodiment.

FIG. 10 is a sequence chart showing the steps of the product purchase supporting method according to the embodiment. The figure shows the steps whereby a prosthetic lower limb user files an application for support to pay for purchase of a prosthetic lower limb with a government. When a prosthetic lower limb user files an application with the government for support to pay for the purchase of a prosthetic lower limb desired to be purchased (S50), the government examines whether to accept the application or not (S52). In the case a plurality of prosthetic lower limb candidates are requested (Y in S54), the government examines all of the candidates. When none of the candidates applied for is accepted (N in S54), the prosthetic lower limb user requests the analysis device 400 for a further proposal of a prosthetic lower limb to purchase (S56). The analysis device 400 returns to S32 of FIG. 9, re-selects an artificial knee joint product recommended to the prosthetic lower limb user (S32), generates a report (S34), and makes a further proposal to the prosthetic lower limb user (S36). In response to the further proposal by the analysis device 400, the prosthetic lower limb user re-determines an artificial knee joint desired to be purchased (S40), and files an application for support to pay for the purchase with the government for a second time (S50). When the application is accepted (Y in S52), the prosthetic lower limb user orders the accepted prosthetic lower limb from the prosthetic limb factory (S64), and the prosthetic limb factory orders the artificial knee joint from the manufacturer (S66). When the artificial knee joint is shipped from the manufacturer, the prosthetic limb factory assembles the prosthetic lower limb (S70) and delivers the prosthetic lower limb to the prosthetic lower limb user (S72). This allows the prosthetic lower limb user to purchase a prosthetic lower limb suited to the user, receiving the support to pay for the purchase.

Described above is an explanation based on an exemplary embodiment. The embodiment is intended to be illustrative only and it will be understood by those skilled in the art that various modifications to combinations of constituting elements and processes could be developed and that such modifications are also within the scope of the present disclosure.

In the embodiment above, a description was mainly given of a technology of recording and analyzing usage information on functions provided in an artificial knee joint. The above technology is also applicable to: prostheses like an artificial lower leg, hip disarticulation prosthesis, artificial arm, and artificial finger; medical equipment like a pacemaker; welfare equipment like a wheel chair, powered bed, walker, and welfare vehicle; and various electronic devices, communication equipment, and home appliances.

An information recording device according to an embodiment of the present invention includes: an acquisition unit that acquires information related to each of a plurality of functions provided in a product; a storage unit that stores usage information related to use of each of the plurality of functions selected or generated from the information acquired by the acquisition unit; and an output unit that outputs the usage information stored in the storage unit. According to this embodiment, the status of use of a function provided in the product can be adequately known.

The plurality of functions may include a function to support a physical function of a user. The usage information includes the number of times that the function is used, duration for which the function is used, or time when the function is used. According to this embodiment, the status of use of the function for supporting the physical function of the user occurring when the user uses a product provided with the function can be known in an objective and quantitative manner.

The acquisition unit may acquire information sensed for execution of each of the plurality of functions. According to this embodiment, a sensing unit provided in the product can be used to record usage information without adding a feature for obtaining usage information. Therefore, the cost of manufacturing the product is reduced.

The information recording device may further include: a recording unit that selects or generates the usage information for storage in the storage unit from the information acquired by the acquisition unit and records the selected or generated information in the storage unit. According to this embodiment, the data volume of information recorded in the storage unit can be reduced so that the capacity of the storage unit can be reduced and the number of steps required to analyze usage information can be reduced.

The usage information stored in the storage unit may be deleted when the user of the product changes. This embodiment supports a case where a product for which usage information is recorded is leased to a plurality of persons interested in the purchase, by allowing usage information to be recorded for each person interested in the purchase.

The output unit may output the usage information stored in the storage unit to an external communication device, and the external communication device may transmit the usage information output by the output unit to a server. According to this embodiment, a large volume of usage information can be accumulated in the server and subjected to analysis.

The external communication device may further acquire information different from the usage information and transmits the information thus acquired to the server along with the usage information. According to this embodiment, information such as an environment in which the product is used can be additionally factored in to analyze usage information so that the status of use of the function can be known more adequately.

The external communication device may acquire and update a program for selecting or generating the usage information in the recording unit. According to this embodiment, a change in, for example, the specification for analysis can be addressed properly.

In a case where the user uses a plurality of products, the external communication device may transmit the usage information on each of the plurality of products to the server. According to this embodiment, the usage information can be analyzed properly even in the event of a change in the product for which usage information is recorded.

A prosthetic limb according to another embodiment of the present invention includes: a main unit worn on one of limbs of a user; a functional unit that exhibits a function of supporting a physical function of one of the limbs of the user; and an information recording device. The information recording device includes: an acquisition unit that acquires information related to each of a plurality of functions exhibited by the functional unit; a storage unit that stores usage information related to use of each of the plurality of functions selected or generated from the information acquired by the acquisition unit; and an output unit that outputs the usage information stored in the storage unit. According to this embodiment, the status of use of the function of the prosthetic limb can be known adequately.

An analysis system according to still another embodiment of the present invention includes: a usage information acquisition unit that acquires the usage information from the above information recording device; an analysis unit that analyzes the usage information acquired by the usage information acquisition unit; and a presentation unit that presents a result of analysis by the analysis unit. According to this embodiment, the status of use of the function provided in the product can be analyzed and presented adequately.

The presentation unit may be provided in a terminal that can be used by a user of the product, and the usage information acquisition unit and the analysis unit are provided in a server device capable of communicating with the terminal. According to this embodiment, the status of use of the product by a plurality of users can be combined and analyzed.

The analysis unit may analyze the usage information on the user as an individual. According to this embodiment, the status of use by the user as an individual can be known adequately.

The presentation unit may present the usage information. According to this embodiment, the user can check his or her own usage information.

The analysis system may further include a storage device that stores the usage information on a plurality of users. The analysis unit may analyze the usage information on the plurality of users. According to this embodiment, the status of use can be analyzed more adequately by using the usage information on the plurality of users.

The presentation unit may present a comparison between the usage information on the user as an individual and the usage information on a plurality of other users. According to this embodiment, whether the function is necessary or not can be objectively determined by comparing the status of use with the status of use of the function by other users.

The analysis unit may identify a function recommended to the user based on the usage information on the user. According to this embodiment, the function that the user needs can be easily and objectively identified and recommended based on the quantitative status of use of the function.

An information recording method according to still another embodiment of the present invention causes a computer to: sense information related to each of a plurality of functions provided in a product; store, in a storage unit, usage information related to use of each of the plurality of functions selected or generated from the information sensed; and output the usage information stored in the storage unit. According to this embodiment, the status of use of the function provided in the product can be known adequately.

The information recording method may further cause a computer to: analyze the usage information; and present a result of analysis. According to this embodiment, the status of use of the function provided in the product can be analyzed and presented adequately.

A method of supporting purchase of a product according to still another embodiment includes: acquiring usage information recorded when a person interested in a purchase of a product provided with a plurality of functions tries out the product and related to use of each of the plurality of functions; analyzing the usage information; and generating evidence data for proving that the person interested in the purchase needs the function provided in the product, when an application for support to pay for a purchase of the product is filed with an examination authority based on a result of analysis. According to this embodiment, application for support to pay for the purchase of the product can be facilitated. In further accordance with the embodiment, acceptance or non-acceptance of the application for support to pay for the purchase of the product can be objectively determined, based on quantitative evidence data based on a record use of the product.

The method of supporting purchase of a product may further include: acquiring a result of determination from the examination authority; and proposing purchase of another product provided with a different function to the person interested in the purchase, when the application for support to pay for the purchase of the product is not accepted. According to this embodiment, the needs of the user and the result of determination by the examination authority are factored in to make an adequate further proposal so that the convenience for the user can be improved.

What is claimed is:

1. An analysis system comprising:
a usage information acquisition circuit that acquires a usage information related to use of each of a plurality of functions for supporting a physical function of a user provided in a prosthetic limb from an information recording device that stores the usage information selected or generated from an information related to each of the plurality of functions, the usage information including at least one of whether an associated function was used or not, a number of times that the function was used, a time when the function was used, sensed information used to control an associated function, information indicating a usage mode or a status of use of the function, a value of a control variable for controlling the function, and an amount of driving by a driver circuit for controlling the function;
an analysis circuit that analyzes the usage information acquired by the usage information acquisition circuit; and
a presentation circuit that presents a result of analysis by the analysis circuit,
wherein
the analysis circuit identifies a function recommended to the user based on the usage information on the user, and
the presentation circuit is provided outside the prosthetic limb.

2. The analysis system according to claim 1, wherein the usage information acquisition circuit and the analysis circuit are provided in a server device capable of communicating with the terminal.

3. The analysis system according to claim 1, wherein the analysis circuit analyzes the usage information on the user as an individual.

4. The analysis system according to claim 1, wherein the presentation circuit presents the usage information.

5. The analysis system according to claim 1, further comprising:
a storage device that stores the usage information on a plurality of users, wherein
the analysis circuit analyzes the usage information on the plurality of users.

6. The analysis system according to claim 5, wherein
the presentation circuit presents a comparison between the usage information on the user as an individual and the usage information on a plurality of other users.

* * * * *